United States Patent [19]

Russell et al.

[11] Patent Number: 6,080,560
[45] Date of Patent: Jun. 27, 2000

[54] METHOD FOR PRODUCING ANTIBODIES IN PLANT CELLS

[75] Inventors: David R. Russell, Madison; James T. Fuller, Oregon, both of Wis.

[73] Assignee: Monsanto Company, St. Louis, Mo.

[21] Appl. No.: 08/279,772

[22] Filed: Jul. 25, 1994

[51] Int. Cl.[7] .......................... C12N 15/29; C12N 15/82; C12N 15/00; A01H 4/00

[52] U.S. Cl. ................. 435/70.1; 435/172.3; 435/419; 435/468; 435/69.1; 435/69.8; 435/70.1; 435/70.21; 536/23.5; 536/24.1

[58] Field of Search .............................. 435/172.3, 320.4, 435/419, 69.1, 468, 320.1, 69.8, 70.1, 70.21; 536/23.5, 24.1; 800/205

[56] References Cited

U.S. PATENT DOCUMENTS

| | | |
|---|---|---|
| 4,816,397 | 3/1989 | Boss et al. . |
| 4,816,567 | 3/1989 | Cabilly et al. . |
| 4,940,840 | 7/1990 | Suslow et al. ........................ 455/69.51 |
| 4,956,282 | 9/1990 | Goodman et al. ................... 435/69.51 |
| 5,102,796 | 4/1992 | Hall et al. ............................. 435/172.3 |
| 5,202,422 | 4/1993 | Hiatt et al. . |

FOREIGN PATENT DOCUMENTS

| | | |
|---|---|---|
| 0 449 375 A2 | 3/1991 | European Pat. Off. . |
| 0 449 376 A2 | 10/1991 | European Pat. Off. . |
| WO 90/02913 | 8/1984 | WIPO . |
| WO 90/02484 | 3/1990 | WIPO . |
| WO 90/02804 | 3/1990 | WIPO . |
| WO 91/02066 | 2/1991 | WIPO . |
| WO 91/06320 | 5/1991 | WIPO . |
| WO 91/13993 | 9/1991 | WIPO . |
| WO 92/01042 | 1/1992 | WIPO . |

OTHER PUBLICATIONS

Hein et al. Biotechnol. Pro. 1991, vol. 7, pp. 455–461.
Hiatt et al. FEBS Letters. Jul. 1992, vol. 307, pp. 71–75.
Fell et al. The Journal of Biological Chemistry. Aug. 1992, vol. 267, No. 22, pp. 1552–1558.
De Loose et al. Gene. 1991, vol. 99, p. 95–100.
Benvenuto, et al., "'Phytoantibodies': a general vector for the expression of immunoglobulin domains in transgenic plants," *Plant Molecular Biology* 17:865–874 (1991).
Bird, R. et al., "Single–Chain Antigen–Binding Proteins," *Science*, 242:423–426 (1988).
Chrispeels, M. J., "Sorting of Proteins in the Secretory System," *Annu. Rev. Plant. Physiol. Plant Mol. Biol.* 42:21–53 (1991).
Denecke, et al., "Protein Secretion in Plant Cells Can Occur via a Default Pathway," *The Plant Cell* vol. 2:51–59 (1990).
During, et al., "Synthesis and self–assembly of a functional monoclonal antibody in transgenic *Nicotiana tabacum*," *Plant Molecular Biology*15:281–293 (1990).
Firek, et al., "Secretion of a functional single–chain Fv protein in transgenic tobacco plants and cell suspension cultures," *Plant Molecular Biology* 23:861–870 (1993).
Hein, et al., "Evaluation of Immunoglobulins from Plant Cells," *Biotechnol. Prog.* 7:455–461 (1991).
Hiatt, et al., "Production of antibodies in transgenic plants," *letters to Nature* 342:76–78 (1989).
Hiatt, A., "Antibodies produced in plants," *Nature* 344:469–470 (1990).
Hiatt, A. C., "Production of Monoclonal Antibody in Plants," *Transplantation Proceedings* , 23:147–151 (1991).
Hiatt, Andrew C., "Monoclonal antibodies, hybridoma technology and heterologous production systems," *Currect Opinion in Immunology* , 3:229–232 (1991).
Hiatt et al., "Monoclonal antiboby engineering in plants," *FEBS* , 307:71–75 (1992).
Hunt et al., "The Signal Peptide of a Vacuolar Protein is Necessary and Sufficient for the Efficient Secretion of a Cytosolic Protein," *Plant Physiol.* 96:18–25 (1991).
Lund et al., "A plant signal sequence enhances the secretion of bacterial ChiA in transgenic tobacco," *Plant Molecular Biology* 18:47–53 (1992).
Owen, et al., "The Expression of Antibodies in Plants," *Chemistry and Industry* , Jun. 1, 1992, pp. 406–408.
Owen, et al., "Synthesis of a Functional Anti–Phytochrome Single–Chain Fv Protein in Transgenic Tobacco," *Bio/Technology* 10:790–794 (1992).
Pang, et al., "Use of the signal peptide of *Pisum vicilin*to translocate β–glucuronidase in *Nicotiana tabacum*," *Gene* 112:229–234 (1992).
Sijmons, et al., "Production of Correctly Processed Human Serum Albumin in Transgenic Plants," *Bio/Technology* 8:217–223 (1990).
Swain, W., "Antibodies in Plants," *Tibtech* 9:107–109 (1991).
Tavladoraki, et al., "Transgenic plants expressing a functional single–chain Fv antibody are specifically protected from virus attack," *Nature* 366:469–472 (1993).

*Primary Examiner*—Lynette R. F. Smith
*Assistant Examiner*—Thomas Haas
*Attorney, Agent, or Firm*—McKenna & Cuneo LLP

[57] ABSTRACT

A method for producing antibodies in plant cells including the steps of providing a genetic construct that encodes a secretable mammalian single chain antibody, delivering copies of the construct into a liquid suspension culture of tobacco cells, selecting for cells that have acquired the genetic construct, allowing the antibody to accumulate in the liquid to a concentration over 25 mg/l and isolating the antibody away from the tobacco cells.

14 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 118 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Nicotiana tabacum (ix) FEATURE:
      (A) NAME/KEY: CDS
      (B) LOCATION: 37..114

(xi) SEQUENCE DESCRIPTION: SEQ ID NO:1:

```
AAGCTTGGAC AACAACTTTT CTCATTTGTT TCAAAG ATG GGA AAA ATG GCT TCT         54
                                        Met Gly Lys Met Ala Ser
                                          1               5

CTA TTT GCC ACA TTT TTA GTG GTT TTA GTG TCA CTT AGC TTA GCT TCT        102
Leu Phe Ala Thr Phe Leu Val Val Leu Val Ser Leu Ser Leu Ala Ser
            10              15                  20

GAA AGC TCA GCC ATGG                                                   118
Glu Ser Ser Ala
        25
```

(2) INFORMATION FOR SEQ ID NO:2:

(i) SEQUENCE CHARACTERISTICS:
      (A) LENGTH: 26 amino acids
      (B) TYPE: amino acid
      (D) TOPOLOGY: linear (ii) MOLECULE TYPE: protein (xi) SEQUENCE DESCRIPTION: SEQ ID NO:2:

```
Met Gly Lys Met Ala Ser Leu Phe Ala Thr Phe Leu Val Val Leu Val
  1               5                  10                  15

Ser Leu Ser Leu Ala Ser Glu Ser Ser Ala
            20                  25
```

(2) INFORMATION FOR SEQ ID NO:3:

(i) SEQUENCE CHARACTERISTICS:
      (A) LENGTH: 103 base pairs
      (B) TYPE: nucleic acid
      (C) STRANDEDNESS: double
      (D) TOPOLOGY: linear (ii) MOLECULE TYPE: DNA (genomic)

(ix) FEATURE:

(A) NAME/KEY: CDS
            (B) LOCATION: 37..99

(xi) SEQUENCE DESCRIPTION: SEQ ID NO:3:

AAGCTTGGAC AACAACTTTT CTCATTTGTT TCAAAG ATG GGA AAA ATG GCT TCT        54
                                        Met Gly Lys Met Ala Ser
                                         1               5

CTA TTT GCC ACA TTT TTA GTG GTT TTA GTG TCA CTT AGC TTA GCC             99
Leu Phe Ala Thr Phe Leu Val Val Leu Val Ser Leu Ser Leu Ala
            10              15                  20

ATGG                                                                   103

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Lys Met Ala Ser Leu Phe Ala Thr Phe Leu Val Val Leu Val
 1               5                  10                  15

Ser Leu Ser Leu Ala
            20

(2) INFORMATION FOR SEQ ID NO:5:

(i) SEQUENCE CHARACTERISTICS:
        (A) LENGTH: 758 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..758

(xi) SEQUENCE DESCRIPTION: SEQ ID NO:5:

ATG GCC GCA TCT AGA CAA ATT GTT CTC TCC CAG TCT CCA GCA ATC CTG        48
Met Ala Ala Ser Arg Gln Ile Val Leu Ser Gln Ser Pro Ala Ile Leu
 1               5                  10                  15

TCT GCA TCT CCA GGG GAG AAG GTC ACA TTG ACT TGC AGG GCC AGC TCA        96
Ser Ala Ser Pro Gly Glu Lys Val Thr Leu Thr Cys Arg Ala Ser Ser
                20                  25                  30

AGT GTA AGT TTC ATG AAC TGG TAC CAG CAG TGT CCA GGA TCC TCC CCC       144
Ser Val Ser Phe Met Asn Trp Tyr Gln Gln Cys Pro Gly Ser Ser Pro
            35                  40                  45

AAA CCC TGG ATT TAT GCC ACA TCC AAT TTG GCT TCT GGA GTC CCT GGT       192
Lys Pro Trp Ile Tyr Ala Thr Ser Asn Leu Ala Ser Gly Val Pro Gly
        50                  55                  60

CGC TTC AGT GGC AGT GGG TCT GGG ACC TCT TAC TCT CTC GCA ATC AGC       240
Arg Phe Ser Gly Ser Gly Ser Gly Thr Ser Tyr Ser Leu Ala Ile Ser
65                  70                  75                  80

AGA GTG GAG GCT GAA GAT GCT GCC ACT TAT TAC TGC CAG CAG TGG AAT       288
Arg Val Glu Ala Glu Asp Ala Ala Thr Tyr Tyr Cys Gln Gln Trp Asn
                85                  90                  95

AGT AAC CCA CTC ACG TTC GGT GCT GGG ACC AAG CTG GAG CTG AAA GAG       336
Ser Asn Pro Leu Thr Phe Gly Ala Gly Thr Lys Leu Glu Leu Lys Glu
            100                 105                 110

CTC TCT GGT GGC GGT GGC TCG GGC GGT GGT GGG TCG GGT GGC GGC GGA       384

```
Leu Ser Gly Gly Gly Gly Ser Gly Gly Gly Ser Gly Gly Gly
            115                 120                 125

TCT CTG CAG ATC CAG TTG GTG CAG TCT GGA CCT GAG CTG AAG AAG CCT       432
Ser Leu Gln Ile Gln Leu Val Gln Ser Gly Pro Glu Leu Lys Lys Pro
        130                 135                 140

GGA GAG ACA GTC AAG ATC TCC TGC AAG GCT TCT GGG TAT ACC TTC ACA       480
Gly Glu Thr Val Lys Ile Ser Cys Lys Ala Ser Gly Tyr Thr Phe Thr
145                 150                 155                 160

AAC TAT GGA ATG AAC TGG GTG AAG CAG GCT CCA GGA AAG GGT TTA AAG       528
Asn Tyr Gly Met Asn Trp Val Lys Gln Ala Pro Gly Lys Gly Leu Lys
                165                 170                 175

TGG ATG GGC TGG ATA AAC ACC TAC ACT GGA CAG CCA ACA TAT GCT GAT       576
Trp Met Gly Trp Ile Asn Thr Tyr Thr Gly Gln Pro Thr Tyr Ala Asp
            180                 185                 190

GAC TTC AAG GGA CGG TTT GCC TTC TCT TTG GAA ACC TCT GCC TAC ACT       624
Asp Phe Lys Gly Arg Phe Ala Phe Ser Leu Glu Thr Ser Ala Tyr Thr
        195                 200                 205

GCC TAT TTG CAG ATC AAC AAC CTC AAA AAT GAG GAC ATG GCT ACA TAT       672
Ala Tyr Leu Gln Ile Asn Asn Leu Lys Asn Glu Asp Met Ala Thr Tyr
210                 215                 220

TTC TGT GCA AGA TTT AGC TAT GGT AAC TCA CGT TAC GCT GAC TAC TGG       720
Phe Cys Ala Arg Phe Ser Tyr Gly Asn Ser Arg Tyr Ala Asp Tyr Trp
225                 230                 235                 240

GGC CAA GGC ACC ACT CTC ACA GTC TCC TCA CCC GGG TA                    758
Gly Gln Gly Thr Thr Leu Thr Val Ser Ser Pro Gly
                245                 250
```

(2) INFORMATION FOR SEQ ID NO:6:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Ala Ser Arg Gln Ile Val Leu Ser Gln Ser Pro Ala Ile Leu
 1               5                  10                  15

Ser Ala Ser Pro Gly Glu Lys Val Thr Leu Thr Cys Arg Ala Ser Ser
                20                  25                  30

Ser Val Ser Phe Met Asn Trp Tyr Gln Gln Cys Pro Gly Ser Ser Pro
            35                  40                  45

Lys Pro Trp Ile Tyr Ala Thr Ser Asn Leu Ala Ser Gly Val Pro Gly
        50                  55                  60

Arg Phe Ser Gly Ser Gly Ser Gly Thr Ser Tyr Ser Leu Ala Ile Ser
65                  70                  75                  80

Arg Val Glu Ala Glu Asp Ala Ala Thr Tyr Tyr Cys Gln Gln Trp Asn
                85                  90                  95

Ser Asn Pro Leu Thr Phe Gly Ala Gly Thr Lys Leu Glu Leu Lys Glu
                100                 105                 110

Leu Ser Gly Gly Gly Gly Ser Gly Gly Gly Ser Gly Gly Gly
            115                 120                 125

Ser Leu Gln Ile Gln Leu Val Gln Ser Gly Pro Glu Leu Lys Lys Pro
        130                 135                 140

Gly Glu Thr Val Lys Ile Ser Cys Lys Ala Ser Gly Tyr Thr Phe Thr
145                 150                 155                 160

Asn Tyr Gly Met Asn Trp Val Lys Gln Ala Pro Gly Lys Gly Leu Lys
                165                 170                 175
```

```
Trp Met Gly Trp Ile Asn Thr Tyr Thr Gly Gln Pro Thr Tyr Ala Asp
            180                 185                 190

Asp Phe Lys Gly Arg Phe Ala Phe Ser Leu Glu Thr Ser Ala Tyr Thr
        195                 200                 205

Ala Tyr Leu Gln Ile Asn Asn Leu Lys Asn Glu Asp Met Ala Thr Tyr
        210                 215                 220

Phe Cys Ala Arg Phe Ser Tyr Gly Asn Ser Arg Tyr Ala Asp Tyr Trp
225             230                 235                 240

Gly Gln Gly Thr Thr Leu Thr Val Ser Ser Pro Gly
                245                 250
```

(2) INFORMATION FOR SEQ ID NO:7:

(i) SEQUENCE CHARACTERISTICS:
        (A) LENGTH: 719 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..719

(xi) SEQUENCE DESCRIPTION: SEQ ID NO:7:

```
ATG GCC CAG GTC CAG CTT CAG CAG TCT GGG GCT GAA CTG GCA AAA CCT      48
Met Ala Gln Val Gln Leu Gln Gln Ser Gly Ala Glu Leu Ala Lys Pro
 1               5                  10                  15

GGG GCC TCA GTG AAG ATG TCC TGC AAG GCT TCT GGC TAC ACC TTT ACT      96
Gly Ala Ser Val Lys Met Ser Cys Lys Ala Ser Gly Tyr Thr Phe Thr
            20                  25                  30

AGC TAC AGG ATG CAC TGG GTA AAA CAG AGG CCT GGA CAG GGT CTG GAA     144
Ser Tyr Arg Met His Trp Val Lys Gln Arg Pro Gly Gln Gly Leu Glu
        35                  40                  45

TGG ATT GGA TAT ATT AAT CCT AGC ACT GGG TAT ACT GAA TAC AAT CAG     192
Trp Ile Gly Tyr Ile Asn Pro Ser Thr Gly Tyr Thr Glu Tyr Asn Gln
 50                  55                  60

AAG TTC AAG GAC AAG GCC ACA TTG ACT GCA GAC AAA TCC TCC AGC ACA     240
Lys Phe Lys Asp Lys Ala Thr Leu Thr Ala Asp Lys Ser Ser Ser Thr
 65                  70                  75                  80

GCC TAC ATG CAA CTG AGC AGC CTG ACA TTT GAG GAC TCT GCA GTC TAT     288
Ala Tyr Met Gln Leu Ser Ser Leu Thr Phe Glu Asp Ser Ala Val Tyr
                85                  90                  95

TAC TGT GCA AGA GGG GGG GGG GTC TTT GAC TAC TGG GGC CAA GGA ACC     336
Tyr Cys Ala Arg Gly Gly Gly Val Phe Asp Tyr Trp Gly Gln Gly Thr
            100                 105                 110

ACT CTC ACA GTC TCC TCC GGA GGC GGT GGC TCG GGC GGT GGC GGC TCG     384
Thr Leu Thr Val Ser Ser Gly Gly Gly Gly Ser Gly Gly Gly Gly Ser
        115                 120                 125

GGT GGC GGC GGC TCT CAA ATT GTT CTC ACC CAG TCT CCA GCA ATC ATG     432
Gly Gly Gly Gly Ser Gln Ile Val Leu Thr Gln Ser Pro Ala Ile Met
    130                 135                 140

TCT GCA TCT CCA GGG GAG AAG GTC ACC ATA ACC TGC AGT GCC AGC TCA     480
Ser Ala Ser Pro Gly Glu Lys Val Thr Ile Thr Cys Ser Ala Ser Ser
145                 150                 155                 160

AGT ATA AGT TAC ATG CAC TGG TTC CAG CAG AAG CCA GGC ACT TCT CCC     528
Ser Ile Ser Tyr Met His Trp Phe Gln Gln Lys Pro Gly Thr Ser Pro
                165                 170                 175

AAA CTC TGG ATT TAT ACC ACA TCC AAC CTG GCT TCT GGA GTC CCT GCT     576
Lys Leu Trp Ile Tyr Thr Thr Ser Asn Leu Ala Ser Gly Val Pro Ala
```

```
            180              185              190
CGC TTC AGT GGC AGT GGA TCT GGG ACC TCT TAC TCT CTC ACA ATC AGC      624
Arg Phe Ser Gly Ser Gly Ser Gly Thr Ser Tyr Ser Leu Thr Ile Ser
        195              200              205

CGA ATG GAG GCT GAA GAT GCT GCC ACT TAT TAC TGC CAT CAA AGG AGT      672
Arg Met Glu Ala Glu Asp Ala Ala Thr Tyr Tyr Cys His Gln Arg Ser
    210              215              220

ACT TAC CCA CTC ACG TTC GGT TCT GGG ACC AAG CTG GAG CTC AAG TA       719
Thr Tyr Pro Leu Thr Phe Gly Ser Gly Thr Lys Leu Glu Leu Lys
225              230              235
```

(2) INFORMATION FOR SEQ ID NO:8:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Gln Val Gln Leu Gln Gln Ser Gly Ala Glu Leu Ala Lys Pro
1               5                   10                  15

Gly Ala Ser Val Lys Met Ser Cys Lys Ala Ser Gly Tyr Thr Phe Thr
            20                  25                  30

Ser Tyr Arg Met His Trp Val Lys Gln Arg Pro Gly Gln Gly Leu Glu
        35                  40                  45

Trp Ile Gly Tyr Ile Asn Pro Ser Thr Gly Tyr Thr Glu Tyr Asn Gln
    50                  55                  60

Lys Phe Lys Asp Lys Ala Thr Leu Thr Ala Asp Lys Ser Ser Ser Thr
65                  70                  75                  80

Ala Tyr Met Gln Leu Ser Ser Leu Thr Phe Glu Asp Ser Ala Val Tyr
                85                  90                  95

Tyr Cys Ala Arg Gly Gly Val Phe Asp Tyr Trp Gly Gln Gly Thr
            100                 105                 110

Thr Leu Thr Val Ser Ser Gly Gly Gly Ser Gly Gly Gly Gly Ser
        115                 120                 125

Gly Gly Gly Gly Ser Gln Ile Val Leu Thr Gln Ser Pro Ala Ile Met
130                 135                 140

Ser Ala Ser Pro Gly Glu Lys Val Thr Ile Thr Cys Ser Ala Ser Ser
145                 150                 155                 160

Ser Ile Ser Tyr Met His Trp Phe Gln Gln Lys Pro Gly Thr Ser Pro
                165                 170                 175

Lys Leu Trp Ile Tyr Thr Thr Ser Asn Leu Ala Ser Gly Val Pro Ala
            180                 185                 190

Arg Phe Ser Gly Ser Gly Ser Gly Thr Ser Tyr Ser Leu Thr Ile Ser
        195                 200                 205

Arg Met Glu Ala Glu Asp Ala Ala Thr Tyr Tyr Cys His Gln Arg Ser
    210                 215                 220

Thr Tyr Pro Leu Thr Phe Gly Ser Gly Thr Lys Leu Glu Leu Lys
225                 230                 235
```

(2) INFORMATION FOR SEQ ID NO:9:

(i) SEQUENCE CHARACTERISTICS:
        (A) LENGTH: 166 base pairs
        (B) TYPE: nucleic acid
        (C) STRANDEDNESS: double
        (D) TOPOLOGY: linear -continued

```
        (ii) MOLECULE TYPE: DNA (genomic)

(xi) SEQUENCE DESCRIPTION: SEQ ID NO:9:

AAGCTTGGAC AATCAGCAAT AGTACTACTA CTCCAAGCAA GCATTTTCCT TACAAGTTTG      60

TTTTTCTTGT GATTAATCGA TATGGCTAGC TCAATGTCCC TTAAGCTTGC ATGTGTGGCG     120

GTGTTGTGCA TGGTGGTGGG TGCACCCCTG GCTCAAGGGG CCATGG                   166
```

METHOD FOR PRODUCING ANTIBODIES IN PLANT CELLS

FIELD OF THE INVENTION

The present invention relates generally to the preparation in plant cells of bioactive mammalian proteins and relates, in particular, to a method for obtaining high yield, purified preparations of conformationally intact mammalian antibodies from plant cell cultures.

BACKGROUND OF THE INVENTION

The medical sciences are increasingly turning to purified mammalian antibodies as powerful diagnostic and therapeutic reagents. The ability to exploit the exquisite specificity of particular antibodies for their antigenic determinants has revolutionized the ways in which diseases are described, diagnosed and treated. For example, cancerous cells can be revealed by tagged antibodies directed against the cell-bound products of activated oncogenes. Cultured antibodies directed against unique epitopes on tumor surface antigens have been chemically coupled to cytotoxic agents and administered therapeutically.

Despite dramatic advances in in vitro antibody synthesis, such as the hybridoma method used to produce monoclonal antibodies, it is still relatively difficult to produce commercially acceptable quantities of purified antibody preparations. In particular, existing commercial methods can require large colonies of laboratory animals or large scale cell culture facilities, each of which comes at great expense. Moreover, purification of individual antibodies of interest from animals or from animal cell culture is laborious because many contaminating biomolecules must be removed from the preparation without destroying the conformational integrity and biological activity of the molecules.

As genes that encode desirable antibodies have become more readily available, efforts have shifted away from production in animals and animal cells and toward the goal of obtaining active animal-derived antibodies from plants and plant cell cultures. It is the hope of workers in this field to increase the yield while decreasing the unit cost of purified antibody preparations.

Hiatt and co-workers, using Agrobacterium-mediated gene transfer methods, have separately transferred expressible DNA constructs encoding immunoglobulin light chain genes and heavy chain genes into tobacco plants. After cross-pollinating the resultant transformed plants, $F_1$ progeny plants were obtained, from which functional two-chain antibody molecules were isolated. The antibody accounted for about 1% of total extractable protein. Hiatt and others have also obtained antibody production in a tobacco cell culture after transferring by electroporation a single vector expressing both a heavy chain gene and a light chain gene.

PCT patent application WO 91/02066 discloses the transformation of tobacco suspension culture cells with a recombinant genetic construct encoding a single chain human serum albumin protein molecule fused to a N-terminal plant signal peptide. After transformation of the cells by electroporation, the human protein was detectable in the culture medium at a concentration of 2 ng per 10 microgram (0.02%) of extracellular protein.

Expression of antibody-like single-chain variable region fragment ($sF_v$) proteins that bind antigens has been observed by Owen et al, *Bio/Technology*, 10:790 (1992) in transgenic tobacco plants at about 0.06–0.1% of total soluble protein. The art has expressed frustration at an inability to achieve high yields of the desired antibodies. When the antibody of interest is produced at a low level, it is concomitantly harder to purify the antibody from the plant or plant extract.

DNA encoding $sF_v$ proteins has been cloned upstream from genes encoding a desired effector function, such as a cytotoxin, in place of the natural effector portion of an antibody molecule to create a novel protein fusion gene. This DNA has been expressed at low levels.

SUMMARY OF THE INVENTION

The present invention is summarized in that a method for producing an immunologically active, conformationally intact mammalian antibody molecule in high yield from plant cell cultures includes delivering into tobacco cells in suspension culture an appropriate plant-expressible genetic construct including a signal peptide that directs secretion of the antibody molecule, and recovering the desired antibody molecule produced by the cells. Antibody can be recovered directly from the growth medium in which the transgenic suspension cells are cultured and can be used without renaturation or other efforts to produce a native conformation capable of binding antigen.

The plant-expressible genetic construct encodes a protein that includes a signal peptide portion and a mammalian antibody portion that recognizes an antigen of interest. The signal peptide portion directs secretion of the protein encoded by the genetic construct from the host NT1 cells into the cell growth medium. Using the method disclosed, a higher yield of immunologically active, conformationally intact mammalian antibody is obtained than has been obtained by other methods known to the art.

It is an object of the present invention to provide a method that permits the recovery of commercially useful quantities of immunologically active, conformationally intact mammalian antibody.

Other objects, advantages and features of the present invention will become apparent upon consideration of the following specification.

DETAILED DESCRIPTION OF THE INVENTION

In the present invention, an expressible genetic construct encoding a signal peptide and an antibody gene portion is introduced into a suspension culture of tobacco cells and the signal peptide and antibody gene are transcribed by the cells. The protein encoded by the construct is secreted from the tobacco cells into the growth medium and may be recovered therefrom at concentrations between 25 and 200 mg/l of growth medium. The protein of interest can accumulate to concentrations of higher than 1% of extracellular protein. Preferably the accumulated protein is greater than 10% of the extracellular protein. The protein can accumulate to more than 50% or even more than 80% of the total extracellular protein.

In this patent application an "antibody" or "antibody molecule" is any single chain polypeptide molecule that includes an antigen recognition portion. The antibody can include two variable regions joined together by a linker. The polypeptide can also include a constant portion having an effector function that can be a function associated with naturally occurring antibodies or can be a function encoded by a gene that has been engineered to be adjacent to the genetic material that encodes the antigen recognition portion. The term "antibody" is specifically intended to include the classes of antibody molecules known in the scientific literature as monoclonals, sFv (single chain variable region fragment) molecules, and SCA (single chain antibody) molecules.

Genetic Construct

An expressible genetic construct useful in the present invention includes, in operative 5' to 3' order, a promoter that promotes transcription in the host cells of plant origin, a signal sequence that encodes a peptide that directs secretion of a protein from the host cells, a DNA sequence encoding a secretable, conformationally intact mammalian antibody molecule, and a transcription termination sequence functional in the host cells. The construct may also contain other advantageous features such as an expressible selectable marker gene and a gene encoding a desirable effector function.

The DNA fragment encoding a secretable, conformationally active mammalian antibody gene can be any genomic or cloned DNA fragment, or cDNA, or synthetic DNA molecule capable of encoding an antigen recognition site of interest. The antibody encoded by the coding region may be full-length or truncated. The antibody may, but need not, encode the constant region that would be found in a naturally occurring full-length antibody molecule.

Conformationally active means that the antibody retains antigen-recognition activity after purification. Activity includes any in vitro or in vivo immunological activity including activities useful in diagnostics and therapeutics.

In nature, the antigen recognition site is encoded in part by a light chain and in part by a heavy chain, each of which includes variable and hypervariable regions which are together responsible for generating antibody diversity. It is well known that these regions of antibody light and heavy chain genes are prone to rearrangement and hypermutation during B-cell development. In addition, the ability of any mature light chain to combine with any mature heavy chain permits a virtually infinite number of antigen recognition sites to be formed, thereby facilitating the ability of the mammalian immune system to recognize with exquisite specificity an astounding number and variety of antigens.

It is possible using techniques known in the art to obtain germline or rearranged genetic material that encodes a desired antigen recognition site from a clonal population of cells. The art is well versed in techniques for generating clonal populations of B-cells or hybridoma cells that overproduce an antibody that recognizes a particular antigen. It is also intended that the antibody coding region for use in the present invention could also be provided by altering existing antibody genes using standard molecular biological techniques that result in the rearrangement, deletion, insertion, or substitution of one or more amino acids in the antibody produced.

The antibody coding region is preferably a genetically-engineered single chain fragment that encodes an antigen-binding variable region, or variants of such fragments. Such fragments, which include covalently-linked portions of both a heavy chain gene and a light chain gene, have been described by Bird et al., "Single-Chain Antigen-Binding Proteins," *Science* 242: 423–426 (1988) and by others. The heavy and light chain variable domains of single chain antibody fragments are joined together by a peptide linker. Genes encoding single chain antigen-binding fragments are typically incorporated in a genetic construct so as to encode an antigen-recognition portion of a fusion protein having a desired enzymatic activity in a host cell. The desired enzymatic activity is encoded by an effector gene fused in-frame to the gene encoding the antigen-recognition portion of the fusion protein. A wide variety of effector genes are known. The genes encoding the recognition and effector portions of the fusion protein can be complete coding regions obtained from wild-type genes, or may be mutant genes, relative to the naturally occurring forms of the genes. The genes utilized may be obtained from genomic DNA or from cDNA clones, may be synthesized in vitro or may be constructed in vitro from parts of other genes. Mutant genes may also be constructed to modify the nucleic acid and/or amino acid sequences as may be desired to modulate a particular function or activity encoded by the particular gene. Known techniques for introducing fine scale changes into known nucleic acid sequences include PCR mutagenesis.

Alternatively, the antibody molecule encoded by the genetic construct may be encoded as two separate DNA segments encoding separate portions of a single complete antibody molecule, such as a light chain gene and a heavy chain gene, under independent transcriptional control. In this case, the two protein chains encoded by the genetic construct combine in the cell to form a secretable functional antibody molecule having antigen recognition and/or effector functions.

The promoter for both the antibody-encoding gene or genes may be any promoter known to be active in plant host cells. Known plant promoters have generally been shown to work well in a variety of plant host cells. Thus, it is believed that any of the known plant promoters would be acceptable for use in the present invention. The promoter need not necessarily be derived from a plant gene, but may also be obtained from a virus or may be synthesized in vitro. The promoter may be inducible or constitutive. Examples of useful promoters are the Cauliflower Mosaic Virus 35S (CaMV 35S) and 19S (CaMV 19S) promoters and the nopaline synthase promoter (nos).

The terminator for both the antibody-encoding gene or genes may, likewise, be any sequence known to be active in plant cells that causes the addition of a poly A chain to mRNA. A suitable terminator is the nopaline synthase poly A addition sequence (nos polyA).

The signal sequence that directs secretion of the antibody protein from the host cell may be any DNA segment that confers upon the antibody product the ability to be translocated across the cell membrane such that the product accumulates at high levels in the culture medium. If the signal sequence causes direct protein translocation, it is provided 5' to the antibody gene coding region. It is also envisioned that the antibody may be secreted from the host by vacuolar translocation. In such a case, the signal sequence can be 5' or 3' to the antibody coding region. The tobacco 5' extensin signal sequence is a preferred signal sequence for use in tobacco cells since its behavior in such cells has been well characterized and since its nucleotide sequence has been published. De Loose, M. et al., *Gene,* 99:95–100 (1991). Sufficient quantities of the tobacco extensin signal sequence may be obtained for cloning into the DNA construct by subjecting tobacco genomic DNA to PCR amplification using primers that flank the signal sequence characterized by De Loose. Two preferred PCR-generated fragments are shown as SEQ ID: 1 and SEQ ID: 3, which encode 26 amino acids and 21 amino acids, respectively, from the 5' end of the tobacco extensin gene. When the 26 amino acid long signal sequence is placed 5' to an antibody coding region, the entire signal sequence is cleaved during peptide maturation precisely at the junction between the signal and the initial methionine of the antibody molecule. The 21 amino acid form of the signal sequence cleaves the mature peptide after amino acid number 2 in the mature protein, thus generating a truncated form of the antibody. These two signal sequence fragments, which could alternatively be synthesized in vitro, can be provided conveniently as HindIII-NcoI fragments which make them amenable to insertion into the DNA construct.

The expressible selectable marker gene, if any, may be any gene that confers a selectable property upon the plant host cells. The marker gene is preferably a gene that confers antibiotic resistance on the otherwise antibiotic-sensitive host cells. Many such genes are known. An APHII gene conferring kanamycin resistance is a suitable selectable marker gene, although other genes that confer kanamycin resistance or resistance to another drug such as neomycin may be used. The selectable marker gene is preferably provided to the genetic construct as a single DNA fragment that includes, in addition to the structural gene, a promoter active in plant cells and a terminator sequence for adding a poly A chain to the marker gene mRNA. The promoter and terminator may be any of those known to the art that confer an acceptable level of resistance so that cells that have taken up the genetic construct may be identified and distinguished from untransformed cells. The regulatory elements that direct expression of the antibody encoding gene or genes may also direct expression of the selectable marker gene.

In the accompanying examples, the exemplary genetic construct includes a gene encoding a tobacco 5' extensin or cotton signal sequence, and an sFv antigen recognition sequence under the transcriptional control of a CaMV 35S promoter and an nos poly A addition sequence.

Host Cells

The genetic construct of the present invention may be transferred into any host cell of plant origin in which the construct is expressible and secretable and from which the desired antibody molecules are secreted at concentrations higher than 25 mg/l of culture fluid. The construct is preferably transferred into a suspension culture of plant cells to facilitate recovery of the secreted protein of interest from the culture medium. Tobacco suspension culture cells are a preferred host. The tobacco cell suspension culture is advantageous in that proteins secreted from suspended cells are released directly into the culture medium, where they may be recovered in high yield. Since the ability to produce callus and to regenerate tobacco plants from cells of a tobacco suspension culture are also known, one may, instead, utilize genetically transformed cells as callus or as regenerated plants. A suitable, and high yielding, host cell line is known as NT1. NT1 cells were reportedly originally developed from N. tabacum L.cv. bright yellow 2. NT1 is a widely used and available cell line freely passed among academic and industrial researchers. The origins of the cell line are obscure. In addition, the cell line is quite mutable and appears to change characteristics in response to culture conditions. Thus, although any tobacco cell suspension culture system can work within the present invention, to enable others to re-create the system described here, a culture of NT1 cells has been deposited under the terms of the Budapest Treaty with the American Type Culture Collection, Rockville, Md. The accession number assigned the deposited NT1 culture was _____.

DNA Transfers

A variety of systems have been used by the present inventors to introduce the DNA constructs described into plant cells. DNA transfer may be Aqrobacterium-mediated, may be by an accelerated particle delivery method or a cell fusion method, an electroporation method, or by any other method for delivering DNA in an expressible form into a host cell.

A preferred DNA transfer method is accelerated particle delivery. The method published by Russell, J. et al., *In Vitro Cell. Dev. Biol.*, 28P:97–105 (1992) and the method of An, G., *Plant Physiol.*, 79:568–570 (1985) have been successfully used to deliver genetic constructs described herein into tobacco cells in suspension culture. The transfer protocol is detailed in the Examples. It is understood that modifications of this protocol are within the ability of one skilled in the art.

Protein Purification

Depending upon the level of purity desired, any known technique for purifying the proteins of interest from the culture medium after secretion may be used. Such techniques can include affinity purification, and electrophoresis.

However, because the antibody protein secreted accounts for such a high proportion of the total extracellular protein (as high as 80%) the protein may, for certain applications, be used without further purification from other proteins. The percent specific yield, and the concentration of desired protein, in this system are markedly higher than those reported in the art where the desired protein has typically been reported at much less than 1% of soluble protein in the culture media.

After the protein has been isolated and, if necessary, purified, it may be used in the same ways as natural antibody proteins. The antibody, may be used in any immunological assay, such as ELISA or Western Blot, or immunological therapy, such as anti-tumor treatments. Thus the present invention provides a desirable high-yield source of animal antibodies without requiring in vivo or in vitro culture of animal cells.

The invention is further clarified by consideration of the following example, which is intended to be purely exemplary of the method of the present invention. Between about 25 and 200 mg of a mammalian antibody are isolated per liter of a transgenic tobacco cell suspension culture. The antibody proteins produced can account for as much as 80% of the protein in the culture medium.

EXAMPLES

Signal Sequences 1. ext26. A 26 amino acid long signal sequence from the 5' end of the tobacco extensin gene was obtained by PCR from tobacco genomic DNA. The tobacco extensin gene was described by De Loose, et al., *Gene*, 99:95–100 (1991), although this paper did not define the extent of the signal sequence. The PCR product was cloned as a HindIII-NcoI fragment and sequenced. The DNA sequence of ext26 is shown as SEQ ID NO: 1. The 26 amino acid signal sequence is shown in SEQ ID NO: 2. The inventors herein disclose that when incorporated in-frame into an expressible genetic construct with an sFv gene, ext26 encodes a signal peptide that is cleaved from the mature protein precisely at the junction between the signal peptide and the ATG start codon of the sFv gene.

2. ext21. A second signal sequence from the tobacco extensin gene that encodes a 21 amino acid long signal peptide was also cloned on a HindIII-NcoI fragment for use in other plasmids. The DNA sequence of ext21 is shown as SEQ ID NO: 3. The 21 amino acid sequence is shown in SEQ ID NO: 4. When incorporated in-frame into an expressible genetic construct with an L6 sFv gene, ext21 encodes a signal peptide that is cleaved from the mature protein after amino acid number 23. Thus a 2 amino acid deletion from the amino terminus of the L6 sFv protein results. It is believed, therefore, that the length of the signal peptide is important for obtaining the desired mature protein.

3. GK12. A signal peptide from a cotton gene was also tested. The DNA encoding the cotton signal peptide GK12 was obtained from a cDNA clone that appears to encode a protein homologous to a class of plant peptide called Lipid Transfer Protein (LTP). The DNA sequence encoding the GK12 signal peptide is shown at SEQ ID NO: 9.

Single Chain Antibody Genes

DNA encoding two single chain versions of the chimeric L6 anti-tumor antibody was separately prepared. Chimeric L6 anti-tumor antibody binds to a cell surface antigen expressed by many human carcinomas. Fell, et al., "Chimeric L6 Anti-tumor Antibody," *J. Biol. Chem.*, 267:15552–8 (1992). The DNA sequence of the L6 sFv portion is shown in SEQ ID NO: 5. The protein encoded by SEQ ID NO: 5 is shown as SEQ ID NO: 6.

Both versions, L6 sFv and L6 cys sFv, recognize human carcinomas. The two versions differ from each other only at nucleotides 145–147. The L6 sFv sequence at nucleotides 145–147 is AAA. In the L6cys sFv, the sequence is TGT. At the protein level, L6 cys sFv includes a cysteine in place of a lysine at amino acid position number 49. Both versions of the single chain antibody gene yielded similar results in the examples below. The majority of the L6-related data were collected using L6 cys sFv. Polyclonal antisera that recognize the L6 antibody as well as anti-idiotype antibodies that only recognize the two single chain forms in their native conformation were described by Hellstrom, et al., "Epitope Mapping and Use of Anti-Idiotypic Antibodies to the L6 Monoclonal Anticarcinoma Antibody," *Cancer Research*, 50:2449–2454 (1990).

An anti-TAC sFv signal chain antibody gene, whose product recognizes a portion of the IL2 receptor, was also transferred into suspension cell cultures. The anti-TAC sFv was derived from a construct encoding an sFv-Pseudomonas exotoxin protein described in *Nature* 339:394–397 (1989) and in *J. Biol. Chem.*, 265:15198–15202 (1990). The Pseudomonas exotoxin portion of the gene fusion was deleted and appropriate transcription signals were added to allow expression of the sFv alone. The sFv retained its ability to recognize the IL2 receptor. The anti-TAC sFv encoding gene sequence is shown as SEQ ID NO: 7. The protein encoded by the gene is shown as SEQ ID NO: 8.

Plasmids

All plasmids described herein were constructed using standard genetic engineering techniques. Constructs were engineered on pUC19 vector backbones. Each included in aphII selectable marker gene in an expressible cassette under the transcriptional control of the nos promoter and soybean poly A addition sequence.

1. pWRG2509. In 5' to 3' order, this control DNA molecule included a Cauliflower Mosaic Virus 35S promoter (35S) that provided transcriptional control of downstream protein-encoding portions of the molecule and DNA encoding the L6 cys sFv single chain anti-tumor antibody.

2. pWRG2510. In 5' to 3' order, this DNA molecule included the 35S promoter, the DNA sequence encoding the ext26 signal peptide, and the L6 cys sFv DNA fused in-frame to the ext26 DNA.

3. pWRG2618. In 5' to 3' order, this DNA molecule included the 35S promoter, the DNA sequence encoding the ext21 signal peptide, and the L6 cys sFv DNA fused in-frame to the ext21 DNA.

4. pWRG2778. In 5' to 3' order, this DNA molecule included the 35S promoter, the DNA sequence encoding the cotton GK12 signal peptide, and the L6 cys sFv DNA fused in-frame to the GK12 DNA.

5. pWRG2835. In 5' to 3' order, this DNA molecule included the 35S promoter, the DNA sequence encoding the ext26 signal peptide, and the anti-tac sFv DNA fused in-frame to the ext26 DNA.

Transfer of DNA Constructs into Tobacco Suspension Cells

Tobacco NT1 cells were grown in suspension culture according to the procedure described in Russell, J., et al., *In Vitro Cell. Dev. Biol.*, 28P:97–105 (1992) and An, G., *Plant Physiol.*,79:568–570 (1985). Briefly, NT1 cells were inoculated into fresh tobacco suspension medium four days prior to gene transfer. On the day of transfer, early log phase cells were plated onto 15 mm target disks in medium containing 0.3 M osmoticum and were rested for one hour. Tobacco suspension medium contains, per liter, 4.31 g of M.S. salts, 5.0 ml of WPM vitamins, 30 g of sucrose, 0.2 mg of 2,4-D (dissolved in KOH before adding). The pH of the medium is adjusted to pH 5.8 with KOH/HCl before autoclaving. Kanamycin is added into the medium at 350 mg/l.

DNA constructs were then transferred into the NT1 suspension cell culture as follows. The DNA construct was delivered into the plated target tobacco cells using a spark discharge particle acceleration device as described in U.S. Pat. No. 5,120,657, which is incorporated herein by reference. Delivery voltages were in the range of 12–14 kV.

After transfer, the target disks were held in the dark for 2 days, during which the medium was changed twice to gradually return the osmoticum to the normal range. The cells were then grown into callus on solid selective medium containing kanamycin for 3–12 weeks with weekly transfers of fresh medium. The callus that formed was returned to suspension after about 3–6 weeks, and the medium was changed weekly.

Secreted peptides were detected in the growth media as follows. After delivery of each DNA construct into tobacco suspension cells, the expression levels of L6 cys sFv were observed by measuring by ELISA using anti-idiotype antibody 13B which detects L6 antibody in its native conformation. Anti-TAC sFv was quantified by coomassie blue staining and was determined to be the desired, properly processed protein by amino acid sequencing. Total secreted protein was measured using the Biorad protein determination assay.

| DNA construct | Expression |
| --- | --- |
| pWRG2509 | <1 mg/l |
| pWRG2510 | 200 mg/l |
| pWRG2618 | 25 mg/l |
| pWRG2778 | 45 mg/l |
| pWRG2835 | 100 mg/l |

These results demonstrate the high yields that may be obtained when plasmids encoding single chain antibody genes are transferred into NT1 cells. These data also demonstrate that while a suitable signal sequence is required, it can be obtained from the tobacco extensin gene, a cotton gene, or, by extension, any other plant signal sequence that causes secretion of proteins from host cells. Moreover, it has also been demonstrated that high protein yields can be obtained with various coding regions. Therefore, the invention is not limited to the particular genes or signal sequences tested.

It is to be understood that the present invention is not limited to the particular embodiments disclosed in this application, but embraces all such modified forms thereof as come within the scope of the following claims.

What is claimed is:

1. A method for obtaining a conformationally active mammalian antibody from plant cells in culture, comprising the steps of:

provided an expressible DNA construct comprising an expressible selectable marker gene and, in 5' to 3' order, a promoter that promotes transcription in tobacco cells in cell culture, a plant signal sequence that encodes a peptide that directs secretion of a protein from the tobacco cells, a DNA sequence that encodes a secretable mammalian single chain antibody, and a transcription terminator functional in the tobacco cells;

transforming tobacco suspension cells with the DNA construct;

selecting for transgenic tobacco cells that have acquired the selectable marker of the DNA construct;

culturing the transgenic tobacco cells in a liquid suspension culture under conditions such that the cells secrete the mammalian single chain antibody encoded by the DNA construct into the liquid culture to a concentration over 25 mg/l, the accumulated mammalian single chain antibody comprising more than 10% of the total secreted protein in the medium; and isolating the accumulated single chain mammalian antibody away from the tobacco cells.

2. A method as claimed in claim 1 wherein the signal sequence is a tobacco extensin signal sequence.

3. A method as claimed in claim 2 wherein the signal sequence is 26 amino acids long.

4. A method as claimed in claim 2 wherein the signal sequence is 21 amino acids long.

5. A method as claimed in claim 1 wherein the signal sequence is a cotton GK12 signal sequence.

6. A method as claimed in claim 1 wherein the secretable mammalian single chain antibody recognizes an IL2 receptor antigen.

7. A method as claimed in claim 1 wherein the secretable mammalian single chain antibody recognizes a human tumor cell antigen.

8. A method as claimed in claim 1 wherein the promoter is a Cauliflower Mosaic Virus 35S promoter, the signal sequence is a 26 amino acid long signal sequence from a tobacco extensin gene, and the secretable mammalian single chain antibody is a variable region that recognizes an IL2-receptor antigen.

9. A method as claimed in claim 1 wherein the promoter is a Cauliflower Mosaic Virus 35S promoter, the signal sequence is a 26 amino acid long signal sequence from a tobacco extensin gene, and the secretable mammalian single chain antibody is a variable region that recognizes a human tumor cell antigen.

10. A method as claimed in claim 1 wherein the delivering step comprises the steps of coating the DNA construct onto carrier particles, and accelerating the coated particles toward the tobacco cells such that some of the coated particles are delivered into some of the cells.

11. A method as claimed in claim 1 wherein the accumulated antibody comprises 10% or more of the total secreted protein.

12. A method as claimed in claim 1 wherein the tobacco cells are NT1 cells.

13. A method for preparing a conformationally active single chain mammalian antibody, comprising the steps of:

transforming NT1 tobacco suspension cells with a DNA construct, the DNA construct comprising an expressible selectable marker gene and, in 5' to 3' order, a Cauliflower Mosaic Virus 35S promoter, a signal sequence selected from the group consisting of a 26 amino acid long signal sequence from a tobacco extensin gene, a 21 amino acid long signal sequence from the tobacco extensin gene, and a signal sequence from a cotton GK12 cDNA clone, a coding region encoding the single chain mammalian antibody, and a transcription terminator functional in the NT1 cells;

selecting for cells expressing the selectable marker gene;

culturing the transformed NT1 tobacco cells in a liquid medium under conditions which allow the single chain mammalian antibody encoded by the DNA construct to accumulate in the liquid to a concentration over 25 mg/l, the accumulated mammalian single chain antibody comprising more than 10% of the total secreted protein in the medium; and isolating the accumulated single chain mammalian antibody away from the NT1 cells.

14. A method as claimed in claim 13 wherein the delivering step comprises the steps of coating the DNA construct onto carrier particles, and accelerating the coated particles toward the tobacco cells such that some of the coated particles are delivered into some of the cells.

* * * * *